United States Patent [19]

Nelson

[11] Patent Number: 4,833,271

[45] Date of Patent: May 23, 1989

[54] STRUCTURALLY DEFINED OLIGOMERS AND PREPARATION THEREOF FOR THE PROTECTION OF OXIDATIVE PHOSPHORYLATION AND WHICH EXHIBIT IONOPHORETIC ACTIVITY

[76] Inventor: George L. Nelson, 4 Iona Ave., Narbeth, Pa. 19072

[21] Appl. No.: 769,045

[22] Filed: Aug. 23, 1985

[51] Int. Cl.$^4$ ............................................. C07C 177/00
[52] U.S. Cl. .................... 562/498; 562/500; 562/503
[58] Field of Search ................. 562/503, 498, 500

[56] References Cited

U.S. PATENT DOCUMENTS 4,153,808  5/1979  Polis ..................................... 560/121

*Primary Examiner*—Robert Genstl
*Attorney, Agent, or Firm*—Prithvi C. Lall; Arthur A. McGill; Michael J. McGowan

[57] ABSTRACT

Structurally-defined, low molecular weight oligomers and preparation thereof which are active in the protection of oxidative physphorylation of mitochondria and exhibit ionophoretic activity. Said structurally defined low molecular weight oligomers are synthesized using a modified 15-dehydro PGB$_1$ such as 16,16-dimethyl-15-dehydro prostaglandin B$_1$ as a precursor to obtain oligomeric mixtures which are structurally defined and active in the protection of oxidative phosphorylation and exhibit ionophoretic activity. Synthesis of modified 15-dehydro-PGB$_1$; 16,16-dimethyl-15-dehydro-prostagalandin B$_1$; is also described.

6 Claims, No Drawings

STRUCTURALLY DEFINED OLIGOMERS AND PREPARATION THEREOF FOR THE PROTECTION OF OXIDATIVE PHOSPHORYLATION AND WHICH EXHIBIT IONOPHORETIC ACTIVITY

STATEMENT OF GOVERNMENT INTEREST

The invention described herein may be manufactured and used by or for the Government of the United States of America for governmental purposes without the payment of royalties thereon or therefor.

BACKGROUND OF THE INVENTION (1) Field of Invention

Subject invention is related to oligomeric mixtures which are active in the protection of oxidative phosphorlyation in degraded mitochondria and exhibit ionophoretic activity. More specifically, this invention relates to the preparation of structurally defined oligomers exhibiting the above activity. It also pertains to structurally modified 15-dehydro-$PGB_1$ compounds useful as precursors for the said oligomeric mixture. This pertains more specifically to the preparation of the structurally modified 15-dehydro-$PGB_1$; i.e. a "C-16 blocked" 15-dehydro-$PGB_1$. This invention also pertains to the reaction conditions required for the conversion of said precursor into oligomeric mixtures from which structurally defined dimers and trimers can be isolated.

(2) Statement of Prior Art

The term $PGB_x$ (i.e., an unknown "x" derived from a prostaglandin B, "PGB") has been rather loosely applied to the reaction mixtures derived from extensive base (hydroxide) treatment of a variety of prostaglandin B precursors as described by Polis et al in *Physiol. Chem. Physics*, 12, 167 (1980) which is incorporated herein by reference. On some occasions, the term PGBx refers to the crude reaction product while at other times it refers to the most active fraction (Fraction 2) derived from size exclusion chromatography of the crude reaction product. Over the last few years, the term PGBx has come to denote a complex mixture derived from treatment of 15-dehydro-prostaglandin $B_1$ (15-dehydro-$PGB_1$) methyl ester, with 1N ethanolic potassium hydroxide. Hereinafter, the term "PGBx" will be referred to the most active fraction derived from the size exclusion chromatography of the crude reaction mixture that results from the treatment of 15-dehydro-$PGB_1$ methyl ester, with 1N ethanolic potassium hydroxide for four hours at 80° C. as will be presently shown in FIG. 1. As will be seen presently in FIG. 2, fraction 2 represents the component exhibiting the maximum biological activity in the protection of oxidative phosphorylation.

A number of unique in vitro and in vivo activities have been demonstrated for certain fractions; i.e., standard PGBx, of the complex mixture derived by ethanolic potassium hydroxide treatment of 15-dehydro-$PGB_1$, as described by Polis et al and Devlin. Standard PGBx protects against the loss of phosphorylating activity during aging in vitro of rat liver mitochondria and functions as a potent "water soluble" ionophore [as indicated by S. T. Ohnishi and T. M. Devlin, Calcium ionophore activity of a prostaglandin $B_1$ derivative (PGBx), *Biochemical and Biophysical Research Communications*, 89, 240 (1979); C. N. Serhan, H. M. Korchak and G. Weissmann; PGBx, a prostaglandin derivative, mimics the action of the calcium ionophore A23187 on human neutrophils, *J. Immunol.*, 80, 2020, (1980); and H. W. Shmukler, Cation complex formation with PGBx, a prostaglandin oligomer, after myocardial infarction with ventricular fibrilation. Effects of PGBx, *Physiol. Chem. Physics*, 12, 81 (1980)] which stimulates the release of $Ca^{++}$ from sacroplasmic reticulum and heart mitochondria. The in vitro activity in the protection of oxidative phosphorylation and ionophoretic activity as demonstrated by Polis et al and Devlin are regarded as predictive of the level of in vivo activity as described below.

In vivo, standard PGBx facilitates and significantly increases survival after what otherwise would be lethal episodes of myocardial ischemia in monkeys and restores nervous system function in dogs after otherwise fatal hypoxia as shown by G. Moss, T. Magliocchetti and R. Quarmby: Immediate restoration of central nervous system autonomic cardiopulmonary control: Survival of "lethal" cerebral hypoxia by treatment with prostaglandin Bx, *Surg. Forum*, 29, 513 (1978) and R. J. Kolata and B. D. Polis, Facilitation of recovery from ischemic brain damage in rabbits by polymeric prostaglandin PGBx, a mitochondrial protective agent, *Physiol. Chem. Physics*, 13, 545 (1981). Standard PGBx also provides a significant measure of protection against the severest forms of cardiac ischemia in various isolated segments of canine heart [as shown by A. P. Walls, N. Himori and A. M. Burkman, Comparison of the effects of prostaglandin Bx (PGBx) and verapamil on changes in myocardial function that occur during schemia, *Proc. Fed. Am. Soc. Exp. Biol.*, Apr. 12, 1980, Atlanta, Ga.] and protects isolated anoxic rat heart as shown by S. T. Ohnishi and T. M. Devlin, Protection by PGBx of isolated anoxic rat heart, in their unpublished results. PGBx appears to represent a class of structures which possess a unique ability to prevent or restore damage on a cellular level due to oxygen deprivation although the mechanism of this action remains unclear. Such unique properties strongly suggest potential future application in treatment of incidents of cerebral and myocardial ischemia and as a therapeutic agent for hemmorragic traumatized combat casualties.

Relatively little from a chemical viewpoint had been conclusively established concerning the structural details of PGBx or the chemistry involved in the formation of the active sites. Earlier descriptions of PGBx as a stable free-radical prostaglandin polymer [as suggested by B. D. Polis, E. Polis and S. Kwong: Protection and reactivation of oxidative phosphorylation in mitochondria by a stable free-radical prostaglandin polymer (PGBx), *Proc. Natl. Acad. Sci. USA*, 76, 1598 (1979)] or even as a polymer derivative of prostaglandin B have been demonstrated to be incorrect upon closer inspection [e.g., G. L. Nelson and G. L. Verdine, The base promoted oligomerization of a 15-dehydro-$PGB_1$. analog: Structural insights into the complex oligomeric mixture termed PGBx, *Tetrahedron Letters*, 23, 1967 (1982) and G. L. Nelson and G. L. Verdine, The base promoted oligomerization of 15-dehydro-prostaglandin B1: Dimer formation and structural implications for a complex mixture termed PGBx. *Tetrahedron Letters* 23, 991 (1983)]. PGBx has been generally characterized on the basis of spectral data as a complex mixture of closely related oligomers formed by an initial reaction at the 13,14-unsaturation of 15-dehydro-$PGB_1$, with the retention of the overall prostaglandin skeleton as described by Polis et al in the reference cited above. Recent attempts by a number of groups to resolve this complex oligomeric mixture into individual components retaining activity have proven unsuccessful precluding a more definitive structural assignment. For example, synthesis and characterization of polymeric derivatives designated PGBx are disclosed in U.S. Pat. No. 4,153,808 issued May 8, 1979 to David Polis et al; synthesis of prostaglandin analogs including ethyl analog; 3-(trans-3-keto-1-pentenyl)-2-cyclopentenone; is disclosed in U.S. Pat. No. 4,338,466 issued July 6, 1982 to George L. Nelson; methods of preparing prostaglandin $B_1$ derivatives are discussed in U.S. Pat. No. 4,245,111 issued Jan. 13, 1981 to Polis et al and conversion of prostaglandin analogs into bicarbonate soluble and bicarbonate insoluble oligomeric mixtures are disclosed in my co-pending patent applications Ser. No. 492,087 U.S. Pat. No. 4,668,828 and 492,088 U.S. Pat. No. 4,663,486 and each with a filing date of May 6, 1983. These two patent applications issued as U.S. Pat. Nos. 4,668,828 and 4,663,486, respectively. All these references are incorporated herein by reference. The lack of any definitive structural detail has hindered the development of a more detailed understanding of the unique biological properties associated with this material. The lack of any definitive structural information limits the development of this material as a useful pharmaceutical agent and thus increases the desirability of this information.

SUMMARY OF THE INVENTION

Structurally defined oligomeric mixtures which are active in the protection of oxidative phosphorylation and exhibit ionophoretic activity and the preparation thereof are taught by subject invention besides a new precursor; a structurally modified 15-dehydro-$PGB_1$; i.e. a "C-16 blocked" 15-dehydro-$PGB_1$, such as 16,16-dimethyl-15-dehydro-prostaglandin $B_1$ and synthesis thereof.

Subject invention further teaches structurally defined dimers and trimers and preparation thereof which exhibit the protection of oxidative phosphorlylation of mitochondria and ionophoretic activity at levels higher than those of the previously described complex and structurally undefined $PGB_x$ as mentioned earlier.

Thus it is an object of subject invention to provide structurally defined oligomeric mixtures that are active in the protection of oxidative phosphorylation of mitochondria and also exhibit ionophoretic activity.

Another object of subject invention is to describe methods for preparing such oligomeric mixtures from structurally modified 15-dehydro-$PGB_1$ derivatives, i.e. a "C-16 blocked" 15-dehydro-$PGB_1$, such as 16,16-dimethyl-15-dehydro-prostaglandin $B_1$ free acid.

Still another object of subject invention is to provide a structurally modified "C-16 blocked" 15-dehydro-$PGB_1$, i.e., 16,16-dimethyl-15-dehydro-prostaglandin $B_1$ free acid which is useful for the preparation of structurally defined prostaglandin oligomers which exhibit the protection of oxidative phosphorylation of mitochondria and ionophoretic activity.

It is another object of subject invention to provide a method of preparation of a structurally modified "C-16 blocked" 15-dehydro-$PGB_1$; 16,16-dimethyl-15-dehydro-$PGB_1$.

Another object of subject invention is to provide structurally defined prostaglandin dimer and the preparation thereof, which exhibits in vitro the protection of oxidative phosphorlation and ionophoretic activity greater than those of $PGB_x$.

Still another object of subject invention is to provide a method of preparation of a structurally defined prostaglandin trimer and the preparation thereof, which exhibits in vitro the protection of oxidative phosphorylation and ionophoretic activity greater than those of $PGB_x$.

Other objects, advantages and novel features of the invention will become apparent to those skilled in the art from the following detailed description of the invention when considered in conjunction with the accompanying drawings wherein:

BRIEF DESCRIPTION OF THE DRAWINGS

FIG. 1 shows schematically the relationship between 15-dehydro-$PGB_1$ methyl ester, a precursor and the oligomeric mixture $PGB_x$ or biologically active component thereof which is called "standard" $PGB_x$.

FIG. 2 graphically indicates the size exclusion chromatography of the crude $PGB_x$ reaction mixture on Sephadex LH-20 indicating fraction 2 or "standard" $PGB_x$;

FIG. 3 shows a comparison between the structures of the ethyl analog used as a model compound in a model study and 15-dehydro-$PGB_1$ methyl ester;

FIG. 4 graphically shows the separation of the crude oligomeric mixture obtained by treatment of the ethyl analog under mild reaction conditions into oligomeric components by size exclusion chromatography on Sephadex LH-20;

FIG. 5 shows the chromatographic separation of the dimer fraction obtained from size exclusion chromatography into six individual dimers;

FIG. 6 represents the formation of single-addition dimers during the oligomerization of the model compound; i.e., the ethyl analog;

FIG. 7 represents the formation of double-addition dimers during the oligomerization of the ethyl analog;

FIG. 8 shows a scheme of trimer formation during oligomerization of the ethyl analog;

FIG. 9 shows the separation of the crude oligomeric mixture obtained by treatment of 15-dehydro-$PGB_1$ free acid under mild reaction conditions into oligomeric components by size exclusion chromatography on Sephadex LH-20;

FIG. 10 graphically shows the chromatographic separation of the dimer fraction obtained from the size exclusion of the 15-dehydro-$PGB_1$ oligomeric mixture, obtained under mild reaction conditions, into individual dimers;

FIG. 11 shows the reaction scheme for dimer formation during the oligomerization of 15dehydro-$PGB_1$ free acid under mild reaction conditions;

FIG. 12 shows a comparison between the model compound, the ethyl analog and the modified or "C-16 blocked" ethyl analog;

FIG. 13 shows the chromatographic separation of the crude oligomeric mixture obtained by treatment of the "C-16 blocked" ethyl analog under mild reaction conditions into oligomeric components by size exclusion chromatography on Sephadex LH-20;

FIG. 14 graphically shows the chromatographic separation of the dimer fraction obtained in FIG. 13, using size exclusion chromatography, into four individual dimers;

FIG. 15 indicates the reaction scheme for dimer formation during the oligomerization of the modified or "C-16 blocked" ethyl analog;

FIG. 16 shows a comparison between "C-16 blocked" ethyl analog and structurally modified, "C-16 blocked", 15-dehydro-PGB$_1$; 16,16-dimethyl-15-dehydro-PGB$_1$;

FIG. 17 shows the chromatographic separation of the crude oligomeric mixture obtained by treatment of 16,16-dimethyl-15-dehydro-PGB$_1$, a structurally modified "C-16 blocked" 15-dehydro-PGB$_1$, by size exclusion chromatography on Sephadex LH-20.

FIG. 18 shows the chromatographic separation of the dimer fraction, obtained from size exclusion chromatography, into four individual dimers;

FIG. 19 indicates the reaction scheme for dimer formation during oligomerization of the structurally modified "C-16 blocked" 15-dehydro PGB$_1$; i.e., 16,16-dimethyl-15-dehydro-PGB$_1$ FIGS. 20–23 outline the synthesis of the new precursor; the structurally modified or "C-16 blocked" 15-dehydro-prostaglandin B$_1$ free acid; 16,16-dimethyl-15-dehydro-prostaglandin B$_1$ free acid; and FIG. 24 shows $^1$H spectrum of 7-(2-trans-4,4,dimethyl-3-keto-1-octenyl)-5-oxocyclopentyl)-heptanoic acid, 16,16-dimethyl-15-dehydro-PGB$_1$ free acid (compound XXI of FIGS. 21–23).

DESCRIPTION OF A PREFERRED EMBODIMENT

As pointed out earlier, PGB$_x$ appears to represent a class of structures which possesses a unique ability to prevent or restore damage on a cellular level due to oxygen deprivation. Such unique properties strongly suggest its potential future application in treatment of incidents of cerebral, and myocardial ischemia and as a therapeutic agent for hemmorragic traumatized combat casualties. However, the mechanism of this action is still unknown. Synthesis of 15-dehydro-PGB$_1$ which acts as a precursor for oligomeric mixture PGBx or standard PGBx is now well known. Furthermore, synthesis of the ethyl analog which includes at least the structure common to all the prostaglandin B analogs is also well known as described in U.S. Pat. No. 4,338,466 issued July 6, 1982 to George L. Nelson. The approach adopted by the teachings of subject invention starts from the already known synthesis of the model compound (i.e., the ethyl analog) to be used for model studies. As will be presently seen subject approach will include a model study using the ethyl analog and a modified or "C-16 blocked" ethyl analog to study the structure of the oligomers, even though biologically inactive, obtained during oligomerization thereof. The results of the model study will then be used to understand the structure of the oligomers produced using a new precursor; structurally modified or "C-16 blocked" 15-dehydro-prostaglandin B$_1$, i.e., 16,16-dimethyl-15-dehydro-prostaglandin B$_1$ and successfully obtain structure elucidation of the oligomers which are active in the protection of oxidative phosphorylation of degraded mitochondria and exhibit ionophoretic activity.

Referring now to the drawings wherein like numbers designate like parts throughout, FIG. 1 indicates oligomerization of 15-dehydro-PGB$_1$ methyl ester indicated by chemical structure 10 when treated with 1N ethanolic KOH for 4 hours at 80° C. forming a complex oligomeric mixture PGBx designated by numeral 12, for which certain fractions show biological activity in the protection of oxidative phosphorylation of mitochondria and ionophoretic activity. As shown in FIG. 1, PGBx is then separated by using size exclusion chromatography such as standard Sephadex LH-20 chromatography to obtain fraction 2 as the most active component of the crude reaction mixture PGBx and is termed as "standard" PGBx designated by numeral 14. The result of the size exclusion chromatography is shown in FIG. 2 where curve 16 is obtained by plotting ultraviolet (UV) absorption which is a measure of oligomeric concentration versus increasing elution volume representing a chromatogram for PGB$_x$ in methanol collected in 40 tubes of discrete fractions. The portion 18 of curve 16 represents "standard" PGBx which is the most active fraction of the crude mixture. Many of the problems associated with the direct structural elucidation of the complex oligomeric mixture termed PGBx appeared to be related to the inherent complexity of oligomeric mixtures in which the unit is a 20-carbon prostaglandin, 15-dehydro-PGB$_1$; designated by numeral 20. The ethyl analog 22 in FIG. 3 contains substantially fewer carbon atoms than 15-dehydro-PGB$_1$ and it retains the essential conjugated cyclopentenone functionality of 15-dehydro-PGB$_1$ thus leading to the expectation of similar reaction pathways. Consequently, the ethyl analog 22 was used as a model compound to study the reaction pathway leading to oligomerization.

Ethyl analog 22 of FIG. 3 was treated with ethanolic potassium hydroxide (KOH) under very mild conditions which resulted in the conversion to a biologically inactive oligomeric mixture containing dimer through octamer components which were separated by standard Sephadex LH-20 chromatography as shown in FIG. 4 where in curve 24 is a plot of ultraviolet (UV) absorption versus increasing elution volume giving rise to peaks 26, 28, 30, 32 and 34 representing monomer, dimer, trimer, tetramer and pentamer components respectively. The dimer component of the oligomeric mixture, after separation from the higher order oligomers, was further separated into individual dimers using the standard technique of HPLC separation (C-18 reverse phase) wherein curve 40 is a plot between ultraviolet (UV) absorption versus increasing elution volume wherein peaks 42, 44, 46, 48, 50, 52 and 54 respectively represent dimer 1, dimer 2, dimer 3, dimer 4, dimer 5, dimer 6 and a trimer. The structural assignments of the individual dimers, based upon a detailed consideration of spectroscopic data are shown in FIGS. 6 and 7.

The assignment of the dimer structures provides for the first time an insight into the chemical pathway of oligomerization and an understanding of the exceptional complexity of the oligomeric mixture that results. Dimers 1–6 are formed by base catalyzed Michael addition in which two nucleophilic sites (C-10 and C-16) and two acceptor sites (C-13 and C-14) of the ethyl analog are active as shown in FIGS. 6 and 7. The presence of multiple reaction sites coupled with the formation of two new chiral centers for each new bond formed results in the formation of a complicated mixture of structural isomers further complicated by the presence of closely related stereoisomer. Dimers 1–4 are derived from C-10 enolate addition as shown in FIG. 6 wherein molecule 60 enolate react at either C-13 or C-14 of molecule 60 to retain a residual 13,14-unsaturation through which further oligomerization can proceed in a similar manner. As shown in FIG. 7, dimers 5 and 6, result from C-16 enolate initiated double addition at either C-13 of molecule 72 or C-14 of molecule 78.

Dimers 5 and 6 lack a 13,14-unsaturation required for further oligomerization and represent terminal reaction products. The formation of higher oligomers, e.g., dimers to trimers, proceeds in a stepwise fashion by enolate addition to a residual 13,14-unsaturation as shown in FIG. 8 wherein dimers 1 and 2 represented by structure 66 react via C-10 enolate addition to form trimers 82 and 84 by the single addition pathway.

The reaction pathway for oligomer chain formation, as derived from the dimer studies of the ethyl analog, has major implications concerning the structural complexity of PGBx. This is evident when considering the sequence: dimers→trimers→tetramers. Trimers are produced from both C-10 and C-16 enolate addition to either C-13' or C-14' of the residual 13,14-unsaturation of dimers 1-4 as illustrated in FIG. 8 in the case of dimers 1 and 2. The addition of the C-10 enolate of the ethyl analog to either C-13' or C-14' of dimers 1 and 2 gives rise to two structurally isomeric trimers, each having 4 chiral centers. Such trimers, hereafter referred to as Type 1 trimers, retain a residual 13,14-unsaturation which is required for enolate addition to form the next higher oligomer. In contrast, the C-16 enolate addition to either C-13' or C-14' of dimers 1 and 2 by the double addition pathway leads to two structurally isomeric trimers, each having 6 chiral centers. Such trimers, referred to as Type 2 trimers in the following discussion, lack the residual 13,14-unsaturation necessary for further chain growth and represent terminal reaction products.

It is when the complexity arising from multiple reaction sites is considered along with the stereochemical consequences of the formation of two new chiral centers for each unit added to the oligomeric chain, that the complexity of a mixture such as PGBx becomes fully evident. Considering only the formation of Type 1 oligomers, i.e., those retaining a residual 13,14-unsaturation required for further chain growth, the expected complexity increases exponentially with each new unit added to the oligomer chain. For example, the single addition dimers (dimers 1-4, type 1) could be converted to 4 structurally isomeric trimers, each having 4 chiral centers. Each of the structurally isomeric type 1 trimers could exist as 8 pairs ($2^4$ possible stereoisomers) of enantiomers. The Type 1 trimers in turn could lead to 8 structurally isomeric Type 1 tetramers, each having 6 chiral centers. Each of the structurally isomeric tetramers could exist as 32 pairs ($2^6$ possible stereoisomers) of enantiomers. The type 1 tetramer in turn could be converted to 16 structurally isomeric Type 1 pentamers, each having 8 chiral centers. Each of the structurally isomeric pentamers could possibly exist as 128 pairs ($2^8$ possible stereoisomers) of enantiomers. In summary, considering only oligomer chain formation by C-10 enolate addition to either the C-13 or C-14 acceptor sites coupled with the creation of two new chiral centers for each unit added, the ethyl analog 22 could lead to 4 pairs ($2 \times 2^2$) of Type 1 enantiomeric dimers, the dimers to 32 pairs ($4 \times 2^4$) of Type 1 enantiomeric tetramers, the tetramers to 2048 pairs ($16 \times 2^8$) of Type 1 enantiomeric pentamers, the pentamers to 16,384 pairs ($32 \times 2^{10}$) of Type 1 enantiomeric hexamers, etc. as shown in Table 1 below.

TABLE 1

| CONSEQUENCES OF MULTIPLE REACTION SITES (SINGLE ADDITION ONLY) | |
|---|---|
| 4 Dimers | ($2 \times 2^2$) |

TABLE 1-continued

| CONSEQUENCES OF MULTIPLE REACTION SITES (SINGLE ADDITION ONLY) | |
|---|---|
| 32 Trimers | ($4 \times 2^4$) |
| 256 Tetramers | ($8 \times 2^6$) |
| 2,056 Pentamers | ($16 \times 2^8$) |
| 16,384 Hexamers | ($32 \times 2^{10}$) |

(PGBx: Estimated to be in the hexamer-octamer range)

The actual reaction mixture would be considerably more complex due to the presence of the Type 2 (double addition) oligomers derived from the C-16 enolate addition to either C-13 or C-14 as shown in FIG. 7. A similar analysis of the possible number of Type 2 C-16 enolate derived stereoisomers reveals a similar level of complexity; $2 \times 2^4$ dimers, $4 \times 2^6$ trimers, $8 \times 2^8$ tetramers, $16 \times 2^{10}$ hexamers, etc. It becomes evident when considering this level of potential complexity that even if only a fraction of the possible stereoisomers are formed in appreciable yields, the direct structural elucidation of PGBx, estimated to be in the hexamer-octamer range, does not represent a feasible approach.

Recognizing the extremely complex nature of PGBx, alternative approaches to less complicated oligomeric mixtures that retained the biological activity characteristics associated with PGBx were explored. The investigations were designed to take advantage of two critical pieces of information derived from the ethyl analog model studies: (1), the oligomerization reaction is very rapid but can be controlled by use of very mild oligomerization conditions and (2) the oligomerization reaction precedes by Michael addition through multiple nucleophilic and acceptor sites. As a result of these investigations, dimers and trimers with activities greater than those of the complex PGBx were obtained from the oligomerization of 15-dehydro-PGB$_1$ under mild conditions. In addition, a "C-16 blocked" 15-dehydro-PGB$_1$ was designed as a precursor which was oligomerized to even less complicated oligomeric mixtures in which structurally-defined dimers, with in vitro biological activities (i.e., the protection of oxidative phosphorylation of mitochondria and ionophoretic activity) equal to or greater than the complex PGBx mixture were isolated.

Oligomerization of 15-dehydro-PGB$_1$ Under Mild Conditions

The initial approach to the formation of less complicated oligomeric mixtures from 15-dehydro-PGB$_1$ methyl ester involved the use of the mild reaction conditions developed for the ethyl analog. The oligomerization took place under mild conditions to give oligomeric mixtures consisting of principally dimer-tetramer components. However, under such mild conditions the ester functionality was retained in the oligomeric mixture resulting in a product that was inactive in the protection of oxidative phosphorylation of degraded mitochondria. In an effort to avoid the problem completely, an alternate synthesis of 15-dehydro-PGB$_1$ free acid was developed.

The oligomerization of 15-dehydro-PGB$_1$ as the free acid under mild conditions resulted in the conversion to an oligomeric mixture consisting primarily of dimer-tetramer components. FIG. 9 shows curve 90 which is a plot of ultraviolet (UV) absorption versus increasing elution volume with peaks 92, 94, 96 and 98 representing formation of dimers, trimers, tetramers and pentamers respectively and some higher order oligomers. Separation of the mixture by size exclusion chromatography followed by analysis of the oligomer components by T. Devlin of Hahnemann Medical College indicated that dimer, trimer and higher components exhibited biological activities of the same order or higher than those of PGBx. In order to insure that the same oligomerization pathway which was observed for the ethyl analog was operating here, the dimer component was separated by reverse phase HPLC with the results shown in FIG. 10 for dimer components of the oligomeric mixture which is very similar to FIG. 5 wherein the individual components characterized by spectroscopic techniques. As indicated in FIG. 11, the structures of the isolated products indicate the same oligomerization pathway similar to the case of the ethyl analog as shown in FIGS. 7 and 8.

Attention was then focused on the trimer component which was separated into Type 1 and Type 2 trimer fractions. Initial work indicated that the Type 1 trimer was the major component and appeared to generally exhibit higher biological activities. The Type 1 trimer mixture was further fractionated and the initial assay results appeared to indicate that activity was distributed throughout and did not reside with a particular stereoisomer or structure type. An attempt was made to separate this Type 1 trimer fraction into individual components but this proved to be very difficult as would be anticipated from a consideration of the predicted complexity of the Type 1 trimer fraction based on the ethyl analog studies. At this stage of the investigation the results of a parallel study of a "blocked" analog became known and led to a shift of focus to the investigation of "blocked" 15-dehydro-PGB$_1$ derivatives.

Model Studies of "Blocked" Derivatives

The goal of less complicated oligomeric mixtures was approached by attempting to reduce the number of available reaction sites in the Michael addition pathway. The initial approach involved the complete elimination of the C-16 enolate pathway while simultaneously introducing some degree of reactivity differential in the acceptor sites. This approach is illustrated in the use of "C-16 blocked" ethyl analog 100 as shown and compared with ethyl analog in FIG. 12. Since the C-16 carbon in the modified ethyl analog 100 is fully substituted, enolate formation is not possible at the site so that all oligomers previously derived from C-16 enolate addition in the ethyl analog 22 are eliminated. Simultaneously, the increased steric demand of the C-16 site serves to provide an increased steric hinderance to the approach of the sterically demanding C-10 enolate at the C-14 acceptor site. The use of the previously developed mild oligomerization conditions provides low molecular weight, i.e., principally dimer-tetramer, oligomeric mixtures.

The reaction of the "blocked" ethyl analog 100 under mild conditions resulted in the conversion to an oligomeric mixture that could readily be separated into dimers, trimers, etc. as shown in FIG. 14 wherein curve 110 includes peaks 112, 114, 116 and 118 for monomer-, dimer-, trimer-, and tetramer components, respectively. The success of this approach was immediately evident upon examination of the dimer component as shown in FIG. 14. Only three dimers represented by peaks 122, 124 and 124 of curve 126 were present and, when characterized, indicated; (1) the absence of any C-16 enolate derived product of the Type 2 and (2) the attack of the C-10 enolate was preferentially taking place at the less hindered C-13 acceptor site as depicted in FIG. 15. The oligomerization of the "blocked" ethyl analog 100 indicated the realization of the major goals: the formation of a lower molecular weight oligomeric mixture in which one of the nucleophilic pathways was eliminated completely while a differential reactivity in the acceptor sites was simultaneously introduced.

Several other advantages that were derived from the use of the modified ethyl analog or "C-16 blocked" 100 became evident during the course of the investigation of the dimer component. An increased ease in the standard HPLC separation of the individual dimer components was readily apparent due to the decreased number of isomers formed; i.e., only three dimers from "C-16 blocked" ethyl analog were formed rather than the six dimers obtained from the ethyl analog 22. With this increased availability, the individual dimers become attractive as intermediates of "known structure" for conversion to higher oligomers. Based on this availability, methods for the conversion of individual dimers into trimers and tetramer mixtures of much lower complexity were developed. Furthermore, the substituents introduced for the purposes of blocking the C-16 enolate formation provided a marked increase in the crystallinity of the dimers. As a result, the Type 1 dimers as defined earlier could be obtained in crystalline form and the crystal structures were determined. This permitted the previously unavailable correlation of proton and carbon-13 NMR parameters with established stereochemistry in the Type 1 dimers and thus provides the foundation for a full stereochemical assignment of the structurally more complex trimers.

Using the experience gained from the model studies involving the use of a "C-16 blocked" ethyl analog, synthesis of a "C-16 blocked" 15-dehydro-PGB$_1$, e.g., 16,16-dimethyl-15-dehydro-prostaglandin B$_1$, were conducted with successful results. By way of an illustration, structurally defined oligomers and their synthesis for the protection of oxidative phosphorylation of degraded mitochondria and which exhibit ionophoretic activity using a structurally defined new precursor and the synthesis thereof will be described. It will be clearly understood that these examples are by way of illustration only rather than a limitation on the scope of subject invention. It should further be noted that FIG. 16 shows the comparison between "C-16 blocked" 15-dehydro-PGB$_1$ and "C-16 blocked" ethyl analog. Furthermore, FIG. 17 represents a curve 130 of chromatographic separation after the oligomerization of a "C-16 blocked" PGB$_1$ giving rise to peaks 132, 134, 136 and 138 representing respectively monomer, dimer, trimer, tetramer components thereof. Additionally, FIG. 18 represents a curve 140 showing the constituents of the dimer fraction of the biologically active (i.e., in the protection of oxidative phosphorylation of degraded mitochondria and exhibiting ionophoretic activity) oligomeric mixture wherein peaks 142, 144 and 146 represent different dimers. FIG. 19 shows the mode of formation via C-10 enolate addition.

The Synthesis of
16,16-Dimethyl-15-Dehydro-Prostaglandin-B$_1$, a
Structurally Modified ("C-16 Blocked")
15-Dehydro-Prostaglandin-B$_1$ It should be noted that in all structural analyses the conventional spectroscopic notation was followed: IR (infrared) wavelength is expressed in microns ($1\mu = 10^{-6}$ meter) or in wave numbers ($cm^{-1}$); NMR (Nuclear Magnetic Resonance) chemical shift is expressed in parts per million (ppm) on the δ scale; s, d, t, q, m denote spin-spin coupling and mean singlet, doublet, triplet, quartet and multiplet respectively; J denotes the coupling constant expressed in hertz (Hz); 1H, 2H, 3H, etc. denotes the number protons. The structurally modified 15-dehydro-$PGB_1$; 16,16-dimethyl-15-dehydro-prostaglandin-$B_1$ was synthesized and the steps are shown by way of an example in FIGS. 20-23. FIG. 20 schematically indicates two alternate methods of synthesis. However, the method of obtaining the compound designated by XXI in FIG. 20 via compound XVII was preferred over the one via compounds XXV and XXVI.

As shown in FIG. 21, azelaic acid (designated as I in FIG. 21) and preferably of technical grade (mp or melting point 104.5° C.) was recrystallized from water and air-dried 3 days to yield white crystalline azelaic acid (mp 106° C., literature value of 106.5° C.). To prepare ethyl hydrogen azelate (designated as II in FIG. 21) azelaic acid (188 g, 1 mole), diethyl azelate (143 g, 0.58 moles), 50 mL (milliliter) of di-n-butyl ether, and 30 g (25 mL) of concentrated HCl were combined in a 1-liter round-bottom flask. The flask was maintained at 165° C. in an oil bath until the mixture was completely homogeneous. The temperature of the bath was then lowered to 120° C., and 60 mL of 95% ethanol was added through the condenser. The mixture was allowed to reflux for 3 hrs, whereupon an additional 20 mL of 95% ethanol was added and refluxing was continued for an additional 2 hrs. The reaction mixture was allowed to cool, then initially distilled under reduced pressure (water aspirator) and then distillation continued at a lower pressure. Ethyl hydrogen azelate was collected (at 157°-159° C. and 0.35 mm of Hg) to give 115 g (53%) of colorless liquid that turned partially solid upon standing. This material was further purified by spinning-band column distillation to give a white crystalline solid (mp 25°-26° C.): IR (neat) 5.75μ (ester C=O) and 5.87 (acid C=O); NMR ($CDCl_3$) δ 4.15 (q, 2H, $CH_3CH_2O$—) and 10.6 given by

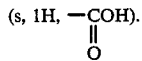

To synthesize ethyl 8-chloroformyloctanoate (designated as III in FIG. 21) a mixture of ethyl hydrogen azelate (II of FIG. 20) (180 g, 0.84 moles) and 145 mL of thionyl chloride (2.0 moles) was placed in a 500-mL round-bottom flask equipped with a condenser connected to an acid trap containing NaOH solution. The mixture was stirred at 60° for 4 hrs and then at 90° C. for 4 hrs. Distillation gave 198 g (85%) of a colorless liquid (bp or boiling point 153°-155° at 1 mm of Hg): IR (neat) 1800 $cm^{-1}$ (acid chloride C=O) and 1730 (ester C=O); NMR ($CDCl_3$) δ 3.9 (q, 2H, —$OCH_2CH_3$), 2.8 (t, 2H, —$CH_2COCl$), 2.3 (t, 2H, —$CH_2COO$—), and 1.2 (t, 3H, —$OCH_2CH_3$).

Ethyl 9-oxodecanoate (designated as IV in FIG. 21) was synthesized wherein magnesium turnings (14.6 g, 0.60 moles) were placed in a 1-L three-necked flask equipped with a mechanical stirrer, a dry-ice condenser with nitrogen inlet, and a water condenser with methyl bromide inlet. After the apparatus had been flamed out under nitrogen, 300 mL of anhydrous ether was added and methyl bromide introduced until all the magnesium had reacted. The rate of methyl bromide addition was controlled to provide a gentle reflux. The Grignard reagent obtained above was cooled in an ice bath, and then 58.5 g (0.32 moles) of cadmium chloride was added in small portions with stirring. The mixture was stirred for 10 min. at room temperature, then heated to reflux. To the refluxing mixture was added dropwise a solution of ethyl-8-chloroformyloctanoate designated as compound III in FIG. 21 (70.3 g, 0.30 moles) in 100 mL of anhydrous ether. When the addition was completed, the reaction mixture was refluxed for 4 hrs. Next, the mixture was cooled in an ice bath, acidified with 10% $H_2SO_4$, and the organic phase separated from the aqueous phase. The aqueous phase was extracted 4 times with 100 mL of ether, each time (hereinafter, abbreviated as 4× with 100 mL of ether). The ether extracts were combined, washed successively with water (4×75 mL), 5% $NaHCO_3$ (3×50 mL), and saturated NaCl (4×75 mL), then dried over anhydrous $MgSO_4$. Distillation through the spinning-band column gave 48.0 g (75%) of a colorless liquid (bp 90°-92° C. at 0.05-0.06 mm of Hg): IR (neat) 1720 $cm^{-1}$ (C=O); NMR ($CDCl_3$) δ 3.9 (q, 2H, $OCH_2CH_3$), 2.0 (s, 3H, —$COCH_3$), and 1.2 (t, 3H, —$OCH_2CH_3$).

To synthesize ethyl 7-(4-ethoxalyl-2,3,5-trioxocyclopentyl)heptanoate (designated as V in FIG. 21), sodium (21 g, 0.94 g-atoms was added to 300 mL of absolute ethanol under nitrogen to prepare a solution of sodium ethoxide. After all the sodium was dissolved (refluxing was required), the solution was cooled and a mixture of ethyl 9-oxodecanoate, (designated as IV in FIG. 21), (59 g, 0.27 moles) and diethyl oxalate (92 g, 0.65 moles) was added dropwise under a nitrogen atmosphere. The reaction mixture was then stirred at room temperature for 1 hr and at reflux for 1 hr. Next, the mixture was cooled and cautiously acidified with ca. (about) 50 mL of 15.6N $H_2SO_4$. The solution was filtered through a layer of Super-Cel (Johns-Manville) to remove the sodium sulfate precipitate incurred by the acidification. The filtrate was concentrated under vacuum and the residue dissolved in 300 mL of ether, then extracted with 5% $NaHCO_3$ (2×200 mL and 5×100 mL). The combined aqueous extracts were acidified with 10% $H_2SO_4$ and extracted with ether (5×200 mL). The ether extracts were dried over anhydrous $MgSO_4$ and the solvent removed under vacuum to yield 96 g (96%) of a reddish viscous product: UV (95% $C_2H_5OH$) 252 and 322 nm (1 nm=1 nanometer=$1\times10^{-9}$ meter); IR (neat) 3300 $cm^{-1}$ (enol OH), 1730 and 1670 (C=O); NMR ($CDCl_3$) δ 10.6 (s, 2H, enol OH) and 4.1 given by

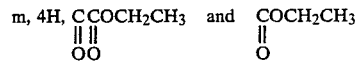

This material was used in the following step without further purification.

For synthesizing ethyl 7-(2,3,5-trioxocyclopentyl)-heptanoate (designated as VI, FIG. 21), a mixture of crude 96 g of ethyl 7-(4-ethoxalyl-2,3,5-trioxocyclopentyl) heptanoate (designated as V in FIG. 21), 200 mL of 95% ethanol and 200 mL of 6N HCl was heated and stirred at reflux (bath temperature 100° C.) for 5 hrs. The reaction mixture was then concentrated under vacuum and the residue extracted with 3×150 mL of ether. The combined ether extracts were washed with 2×75 mL of water, dried over anhydrous MgSO4, and concentrated under vacuum to give a reddish oily product (82 g, 115%): UV maximum (95% ethanol) 266 and 323 nm; IR (neat)3200 cm$^{-1}$ (enol OH), 1730, 1680, and 1650 (C=O); NMR (CDCl3) δ 10.1 (s, 2H, enol OH), 4.2 (q, 2H, —OCH2CH3), and 3.0 (s, 2H, methylene at 4 position).

The next step in subject synthesis, ethyl 7-(2,5-dioxo-3-semicarbazonocyclopentyl)-heptanoate (designated as VII in FIG. 21) was prepared wherein a solution of 82 g of crude trione (designated as VI in FIG. 21) in 300 mL of 95% ethanol, a solution of semicarbazide hydrochloride (42 g, 0.38 moles) and sodium acetate (59 g, 0.72 moles) in 445 mL of water was added with stirring. The reaction mixture was then stirred for 1 hr and diluted with 100 mL of water and allowed to stand overnight. The filtered precipitate was washed with water, then with 3×100 mL of methanol, and dried under vacuum to yield 61 g [68% based on compound V of FIG. 21] of a powdery yellow product (mp 246°-248° C.): IR (nujol) 3350 cm$^{-1}$ (NH), 1760,1710, 1660 and 1605 (C=O).

Furthermore, to synthesize 7-(2,5-Dioxocyclopentyl)heptanoic acid (designated as VIII in FIG. 21), 61 g of the semicarbazone (compound VII of FIG. 21), from the above procedure was added to a 1 liter round-bottom flask containing a solution of KOH (94 g, 1.7 moles) in 366 mL of ethylene glycol. The mixture was gradually heated with stirring to 160° C. over a 1-hr period then refluxed for 6 hrs at 192° C. The solvent was removed under vacuum and the residue dissolved in 150 mL of water. The resulting solution was refluxed for 45 min. After cooling, the solution was acidified with HCl (ca. 150 mL) and filtered. The precipitate was washed with cold water and dried under vacuum to give 38 g (86%) of a powdery light-brown product (mp 120°-125° C.). IR (KBr) 3200-2300 cm$^{-1}$ (enol and acid OH), 1700 (carboxy C=O), 1610 (ketonic C=O), and 1550 [β-diketone (enolic) C=O].

To prepare methyl 7-(2-methoxy-5-oxocyclopentyl)-heptanoate (designated as IX, FIG. 21) crude 7-(2,5-dioxocyclopentenyl)heptanoic acid (VII of FIG. 21) 282 g from the previous step, was combined with 600 mL of methanol, 600 mL of chloroform, and 8 mL of concentrated H2SO4, then refluxed ca. 48 hrs. The reaction product, after cooling, was poured into a mixture of 300 g cracked ice and 1.2 liters of water. The aqueous layer was separated and washed with two additional portions of chloroform. The combined organic extracts were then washed with water. After removal of the chloroform under vacuum, 275 g (94% based on simple esterification) was obtained. This material was used in the following procedure without purification. (b) The crude ester from the above procedure was treated in 30 g portions with ethereal diazomethane generated from 50 g of Diazald (Aldrich Chemical, Milwaukee). After removal of the solvent, ca. 32 g of crude (IX) was obtained.

The crude dark oily (compound IX of FIG. 21) was distilled in 100 g amounts (bp 160°-165° C. at 0.1 mm of Hg) to give 78-80% of a light yellow oil that crystalized upon standing in the freezer: UV max (95% ethanol) 251 nm; IR (neat) 1730 cm$^{-1}$ (ester C=O), 1680 (cyclopentenone C=O), and 1630 (enolic double bond), 1370 nnd 1270 (enol ether); NMR (CDCl3) δ 3.7 (s, 3H, —OCH3) and 3.4 (s, 3H, —COOCH3).

In the next step to prepare 7-(2-methoxy-5-oxocyclopentenyl)heptanoic acid (designated as X, in FIG. 21), a mixture containing 76.3 g (0.3 moles) of methyl-7-(2-methoxy-5-oxocyclopentenyl)heptanoate (IX of FIG. 21), 1.5 L of 95% ethanol, and 3.2 L of 0.1N NaOH (0.32 moles) was stored at room temperature for 2 days. Ethanol was removed under vacuum and the aqueous residue washed with ether. The aqueous solution was then acidified with 0.5N HCl to pH 5 and extracted with ethyl acetate (2×150 mL). The aqueous solution was further acidified to pH 3 and again extracted with ethyl acetate (3×100 mL). The combined ethyl acetate was removed under vacuum. A reddish oily product (70 g, 97%) was obtained: UV max (95% ethanol) 251 nm; IR (neat) 3300-2600 cm$^{-1}$ (acid OH), 1720 (carbonyl C=O), 1603 (enolic double bond), 1370 and 1270 (enol ether); NMR (CDCl3) δ 10.9 (s, 1H, —COOH) and 3.8 (s, 3H, —OCH3).

Additionally, for the synthesis of (2-methylpropylidene)-tert-butylamine (designated as XII in FIG. 22), to a 2-L 3-neck round bottom flask equipped with a thermometer, mechanical stirrer and addition funnel is added 292 grams (4 moles) of tert-butylamine. Isobutyraldehyde (288 grams, 4 moles) is added dropwise at a rate to maintain the reaction temperature between 25°-40° C. The aqueous layer that separates is removed and 60 grams of anhydrous potassium carbonate is added. After stirring overnight, the reaction mixture is decanted onto 48 grams of barium oxide and stirred an additional 12 hours. After filtration, the reaction mixture is distilled at atmospheric pressure with the Schiff base XII collected between 90°-100° C. to give 380 grams (75%); IR (neat) 5.95μ (C=N); NMR (CDCl3) δ 7.39 (d, 1H, J=6 Hz, —CH—CH=N), 1.16 (s, 9H, —C(CH3)3), and 1.03 (d, 6H, —CHC(CH3)2)—.

Furthermore, for the synthesis of N-(2,2-dimethyl hexylidene)-tert-butylamine (designated as XIII, in FIG. 22), a 2-L 3-neck round bottom flask is equipped with a mechanical stirrer, addition funnel with nitrogen inlet, low-temperature thermometer and cooling bath. After drying under nitrogen, the flask is charged with 52.6 g (0.52 mole) of di-isopropylamine and 350 mL of dry tetrahydrofuran. The addition of n-butyl lithium (0.52 mole) is carried out at such a rate as to maintain the internal temperature from −10° C. to −5° C. After completion of the addition, the reaction mixture is stirred for 30 minutes and then 66.2 g (0.52 mole) of Schiff base (designated as XII in FIG. 22) is added dropwise at a rate to maintain the internal temperature between −10° C. to −5° C. After completion of the addition, the reaction mixture is stirred for 90 minutes while the reaction temperature is allowed to rise to 10° C. Then 82 g (0.60 mole) of n-butyl bromide is added dropwise while maintaining the temperature between 20° C. to 40° C. The reaction mixture is stirred overnight and then 1300 mL of brine is added to the reaction mixture and the entire contents transferred to a separatory funnel. The organic layer is separated and the aqueous layer extracted with 3×100 mL of methylene chloride. The combined organic extracts are dried over anhydrous sodium sulfate. After removal of the solvent, the crude product is distilled at 105° C. at 80 mm of Hg to give 139 grams (76%) of alkylated Schiff base (compound XIII of FIG. 22); IR (neat) 5.95μ (C=N); NMR (CDCl3) 7.40δ (s, 1H, —C—CH=N), 1.14 (s, 9H —C(CH3)3), 1.00 (s, 6H, —C(CH3)2—), and 0.95 (t, 3H, —CH2—CH3).

2,2-Dimethylhexanal (designated as XIV, in FIG. 22) was prepared wherein N-(2,2-Dimethylhexylidene)-tert-butylamine (90 g, 0.49 mole) is taken up in 375 mL of hexane and placed in a 3-neck round bottom flask equipped with a mechanical stirrer and nitrogen inlet. To this apparatus is added 945 mL of 1M acetic acid and the heterogeneous reaction mixture is stirred for 3.5 hours. The reaction mixture is transferred to a separatory funnel and the organic layer separated. The aqueous layer is extracted with 3×200 mL of diethyl ether. The combined organic extracts are then washed with 3×150 mL of 10% sodium bicarbonate solution followed by 3×150 mL of brine and dried over anhydrous sodium sulfate. After removal of solvent, the crude products of four hydrolyses were combined to give 258 grams which was distilled to yield 209 grams of compound XIV at 80° C. at 60 mm Hg for an overall yield of 83%; IR (neat) 5.82μ (aldehyde C=O), 3.68 (aldehyde C-H); NMR (CDCl$_3$) 9.44 δ (s, 1H, aldehyde C-H), 1.04 (s, 6H, —C(CH$_3$)$_2$, and 0.89 (t. 3H, —CH$_2$—CH$_3$).

In the preparation of 4,4-dimehtyl-oct-1-yn-3-ol (designated as XV, in FIG. 20), magnesium turnings (30 g, 1.23 moles) were placed in a three-necked round-bottom flask equipped with mechanical stirrer, reflux condenser, and dropping funnel. The flask was flamed out under nitrogen and to it 200 mL of dry tetrahydrofuran was added. Ethyl bromide (120 g, 1.1 moles) was dissolved in 400 mL of dry tetrahydrofuran and this solution was added dropwise to the magnesium turnings. This reaction mixture was heated on the steam bath for 2 hrs. Meanwhile, a 2-L round-bottom flask equipped with stirring bar, inlet tube, and dropping funnel was flamed out under nitrogen and to it was added 600 mL of dry tetrahydrofuran. After the reaction flask was cooled, acetylene was passed through a dry-ice acetone trap and bubbled into the reaction vessel. The previously prepared solution of ethyl magnesium bromide was cooled and rapidly transferred to a 500-mL dropping funnel, and slowly added dropwise to the acetylene solution over a period of 2 hrs; 100 g (1.0 mole) of hexanal (compound XIV of FIG. 22) in 100 mL of dry tetrahydrofuran was then added dropwise with stirring over a period of 1 hr. The addition of acetylene was stopped and the reaction mixture was cooled to room temperature and stirred overnight. A solution of 200 g of ammonium chloride in 100 mL of water was then added gradually to the mixture. The tetrahydrofuran layer was separated, the solvent removed under vacuum, the water layer extracted with 4×100 mL of chloroform, and the combined extracts added to the crude alcohol. The combined material was washed with water until neutral and then dried over anhydrous MgSO$_4$. After removal of the solvent, 164 g of crude alcohol was obtained. On distillation of the crude material, 126 g (82%) of a colorless liquid (bp 35° at 0.2 mm Hg) was obtained: IR (neat) 3.0μ (hydroxyl and acetylene C-H) NMR 4.07 δ given by

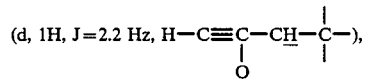

2.44 given by

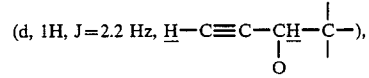

0.95 and 0.96 given by

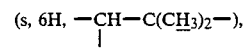

due to chiral center) and 0.90 and 0.92 (t, 3H, —CH$_2$—CH$_3$, due to chiral center).

For the preparation of 2-(4,4-dimethyl-(oct-1-yn-3-loxy)tetrahydropyran (designated as XVI in FIG. 22), concentrated HCl (0.7 mL) was added dropwise with stirring to a mixture of 182 g (1 mole) of 16,16-dimethyl-oct-1-yn-3-ol (compound XV of FIG. 22) and 92 g (1.1 mole) of dihydropyran and allowed to stand at room temperature overnight. The reaction mixture was then diluted with 150 mL of ether, washed with 10% NaHCO$_3$, and dried over anhydrous MgSO$_4$. Removal of the drying agent by filtration and the solvent under vacuum yielded 248 g of crude THP derivative (compound XVII of FIG. 22). On distillation of the crude product, 236 g (99%, bp 125°-130° at 0.4 mm of Hg) of a colorless liquid was obtained: IR (neat) 3.0μ (sharp C≡C-H) and 4.7 (weak C≡C stretch): NMR (CDCl$_3$) δ 4.99 and 4.67 given by: (broadened s, 1H,

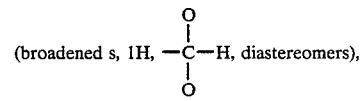

4.01 and 3.85 given by

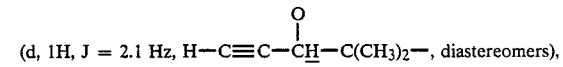

2.40 and 2.39 given by

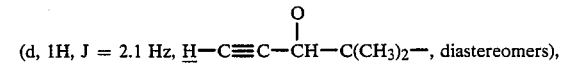

0.98 and 0.95 given by

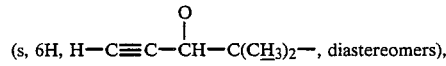

and 0.90 (t, 3H, CH$_2$—CH$_3$).

For synthesizing 7-(2-(3-(tetrahydropyraoxy)-4,4-dimethyl-1-octynyl)-5-oxocyclopentenyl) heptanoic acid, (designated as XVII in FIG. 23), a solution of 2-(4,4-dimethyl-(oct-1-yn-3-yloxy)tetrahydropyran (compound XVI of FIG. 22), 357 g, 1.5 moles) in 500mL of dry tetrahydrofuran was added dropwise 500 mL of 3.0 M ethereal ethyl magnesium bromide (1.5 moles) under nitrogen. The mixture was refluxed for 2 hrs, then cooled in an ice bath. To the Grignard reagent prepared above was added dropwise a solution of 7-(2-methoxy-5-oxocyclopentenyl) heptanoic acid (X, 70 g, ~0.3 moles) in 50 mL of dry tetrahydrofuran under nitrogen. The resulting reaction mixture was stirred overnight at room temperature. The reaction mixture was then poured into one L (liter) of cold water, acidified with 2N HCl, and extracted with ether (4×150 mL). The combined ether layers were washed with 1N NaOH (4×150 mL). The aqueous layers were washed with ether (2×150 mL), acidified with 2N HCl, and extracted with 4×150 mL of ether. The combined ether extracts were washed with 5×100 mL of water and dried over anhydrous MgSO4. The solvent was removed under vacuum. The crude dark reddish oily product (120 g, ca. 90%) was purified by preparative chromatography on C-18 reverse phase using 80/20 CH3C≡N/H2O to provide an overall 65% yield; UVmax (95% ethanol) 269 nm, NMR (CDCl3) δ 5.03 and 4.78 given by

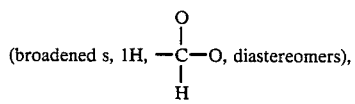

(broadened s, 1H, —C—O, diastereomers), 4.40 and 4.15

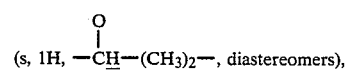

(s, 1H, —CH—(CH3)2—, diastereomers), 1.03 and 1.00

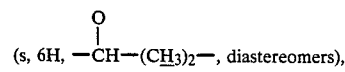

(s, 6H, —CH—(CH3)2—, diastereomers), and 0.91 (t, 3H, —CH2—CH3).

For the synthesis of 7-(2-(4,4-dimethyl-3-hydroxy-1-octynyl)-5-oxocyclopentenyl)heptanoic acid (designated as XVIII in FIG. 23), a mixture containing 110 g of the THP derivative (compound XVII of FIG. 23), 200 mL of tetrahydrofuran, 600 mL of glacial acetic acid, and 200 mL of water was stirred overnight at 50° C. The reaction mixture was added to 2.5 L of cold water, then extracted with a total of 500 mL of chloroform. The combined chloroform extracts were washed with a total of 2 L of water. Removal of the chloroform under vacuum gave 90 g of crude compound XVIII. The crude product was purified by preparative chromatography on C-18 reverse phase using 80/20 CH3C≡N/H2O to give 85% of compound XVIII, with the unreacted THP compound XVIII collected and recycled in a subsequent hydrolysis. Pertinent spectral data for XVIII is as follows:

UVmax (95% ethanol) 270 nm: IR (neat) 3.3μ (—OH); NMR (CDCl3) δ 4.37 given by

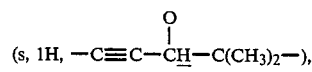

(s, 1H, —C≡C—CH—C(CH3)2—), 0.96 given by

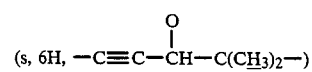

(s, 6H, —C≡C—CH—C(CH3)2—)

and 0.91 (t, 3H, —CH2—CH3).

For the next step in the process was the synthesis of 7-(2-(4,4-dimethyl-3-keto-1-octynyl)-5-oxocyclopentenyl)heptanoic acid (designated as XIX, in FIG. 23), a solution of 5.4 g (0.015 mole) of 7-(2-(4,4-dimethyl-3-hydroxy-1-octynyl)-5-oxocyclopentenyl)heptanoic acid (compound XVIII) in 40 mL of acetone was added to a 100-mL 3-neck round-bottom flask equipped with a stirrer and low-temperature thermometer. The solution was initially cooled to between −10° C. to −15° C. in an ice-methanol bath and the dropwise addition of the Jones reagent was controlled to maintain the reaction temperature between −5° C. to −10° C. The reaction was quenched by the addition of 5 mL of isopropyl alcohol. After dilution with 100 mL of water, the reaction mixture was extracted with 3×50 mL of ether. The combined ether extracts were washed with 3×100 mL of water and dried. The ether was removed at reduced pressure to give 80–90% crude reaction product. The crude ketone (compound XIX) was chromatographed on C-18 reverse phase using 60/40 CH3C≡N/H2O for elution to give a 70% yield of compound XIX: UVmax (95% ethanol) 280 nm; MNR (CDCl3) δ 1.21 given by

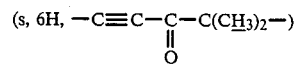

(s, 6H, —C≡C—C—C(CH3)2—)

and 0.97 (t, 3H, —CH2—CH3).

Furthermore, to synthesize 7-(2-(cis-4,4-dimethyl-3-keto-1-octenyl)-5-oxoyclopentenyl)-heptanoic acid (designated as XX in FIG. 23), palladium on barium sulfate (5%, 0.5 g), 0.25 mL of quinoline and 30 mL of methanol were combined in a 500-mL hydrogenation vessel (Joshel apparatus) and equilibrated overnight. A solution of 5.4 g (0.015 mole) of 7-2-(4,4-dimethyl-3-keto-1-octynyl)-5-oxo-cyclopentenyl)heptanoic acid (compound XIX) in 30 mL of methanol was introduced and hydrogenated to 90% of theoretical uptake. The catalyst was removed by filtration and the methanol removed under reduced pressure. The resulting residue was dissolved in 100 mL of ether, then washed with 0.1N HCl (3×30 mL) and water (3×30 mL). After drying, the ether was removed under reduced pressure and this material was combined with the product of similar hydrogenations and purified by preparative chromatography on C-18 reverse phase using 60/40 CH3C≡N/H2O for elution. In this manner, a yield of compound XX of 75–80% was obtained: UVmax 285 nm, NMR (CDCl3) δ 6.74 given by

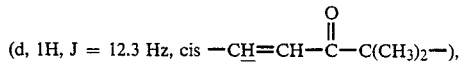

(d, 1H, J = 12.3 Hz, cis —CH=CH—C—C(CH3)2—), 6.58 given by

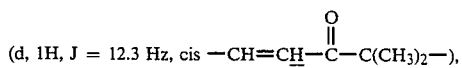

(d, 1H, J = 12.3 Hz, cis —CH=CH—C—C(CH3)2—), 1.16 given by

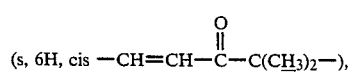

(s, 6H, cis —CH=CH—C—C(CH3)2—), and 0.89 (t, 3H, —CH2—CH3).

The syntheses of 7-(2-(trans-4,4-dimethyl-3-keto-1-octenyl)-5-oxocyclopentenyl)-heptanoic acid (designated as XXI in FIG. 20-23) was accomplished as follows: to a 250-mL round bottom flask containing 200 mL of glacial acetic acid and 2.5 g of KI was added 5.4 g (0.915 mole) of 7-(2-(cis-4,4-dimethyl-3-keto-1-octenyl)-5-oxo-cyclopentenyl)heptanoic acid (compound XX). The reaction mixture was stirred at room temperature and the progress of the cis to trans isomerization was monitored by UV spectroscopy. The reaction mixture was diluted with water and extracted with $CH_2Cl_2$ (3×50 mL). The combined organic extracts were washed thoroughly with $H_2O$ and the solvent was removed under vacuum. The crude reaction products from several isomerizations were combined and purified by preparative chromatography on C-18 reverse phase using 60/40 $CH_3C\equiv N/H_2O$ for elution. In this manner, a 85–90% yield of 7-(2-(trans-4,4-4-dimethyl-3-keto-1-octenyl)-5-oxocyclopentenyl)-heptanoic acid (compound XXI) is obtained: UVmax (95% ethanol) 296 nm: NMR ($CDCl_3$) 7.76δ as given by

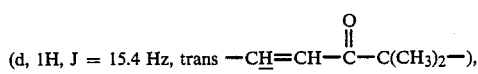

(d, 1H, J = 15.4 Hz, trans $-CH=CH-\overset{O}{\overset{\|}{C}}-C(CH_3)_2-$), 6.95 as given by

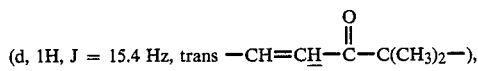

(d, 1H, J = 15.4 Hz, trans $-CH=C\underline{H}-\overset{O}{\overset{\|}{C}}-C(CH_3)_2-$), 1.19 as given by

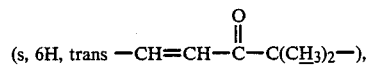

(s, 6H, trans $-CH=CH-\overset{O}{\overset{\|}{C}}-C(C\underline{H}_3)_2-$), 0.88 (t, 3H, $-CH_2-CH_3$). The complete $^1H$ NMR spectrum of 7-(2-(trans-4,4-dimethyl-3-keto-1-octenyl)-5-oxocyclopentenyl)-heptanoic acid (compound XXI) is shown in FIG. 24.

The Preparation of Structurally Defined Oligomeric Mixtures From 16,16-Dimethyl-15-Dehydro-$PGB_1$ To a 500-mL round bottom flask equipped with a stirring bar was added a solution of 2 g of 7-(2-(trans-4,4-dimethyl-3-keto-1-octenyl)-5-oxocyclopentenyl)-heptanoic acid (designated as XXI in FIGS. 20–23) in 100 mL of ethanol (20 mg/mL). To this was added 100 mL 0.1N KOH and the progress of the oligomerization is monitored by UV spectroscopy. When ca. 50% of compound XXI had reacted, usually requiring 60–90 min., the oligomerization reaction was quenched by acidification with 2N HCl. The reaction mixture was diluted with 200 mL of water and extracted with 3×50 mL of $CH_2Cl_2$. The solvent was removed under vacuum to give 2 g of a mixture containing 45% unreacted monomer, 30% dimer, and 20% of trimer with smaller amounts of tetramer and some higher oligomers.

Isolation of Dimer and Trimer Fractions

The crude oligomeric mixtrre obtained by using a "C-16 blocked"-15-dehydro-$PGB_1$, i.e., 16,16-dimethyl-15-dehydro$PGB_1$ as a precursor exhibits the protection of oxidative phosphorylation in degraded mitochondria and ionophoretic activity. This oligomeric mixture is much simpler in structure than the undefined $PGB_x$ and its structure is given by a general structural formula shown below:

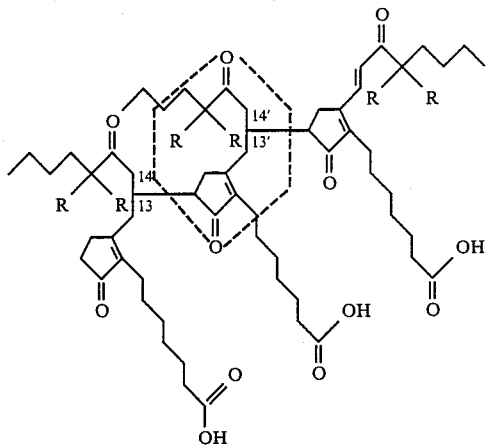

where n=0, 2, 3, . . . When n=0, the above-shown formula represents the dimer fraction of the above-mentioned crude oligomeric mixture. Trimer- and tetramer fractions are represented by the structural formula given above with n=1 and 2, respectively.

The crude oligomeric mixture from above is separated into oligomeric components by chromatography on three 2.54 cm×109 cm columns of Sephadex LH-20 in series using methanol for elution. The separation of this mixture into dimers, trimers and tetramers is illustrated in FIG. 17. This is in complete contrast to the crude oligomeric mixture termed $PGB_x$ in which there is no resolution into oligomeric fractions as shown in FIG. 2.

Dimer Components

The dimer component from above can be resolved into individual dimers by chromatography on C-18 reverse phase as is illustrated in FIG. 18. The structural assignments of the four dimers are given by the structural formula written above for an oligomeric mixture with n=0 for the dimers. This is further illustrated in FIG. 19.

Trimer Components

The trimer component or fraction is anticipated to be a considerably more complex mixture than the dimer component with up to 16 possible structural and stereochemical isomers possible. The general structure of the trimers is given by the general structural formula for the oligomeric mixture with n=1.

Tetramer Components

The tetramer component or fraction of the oligomeric mixture is also very complex with the general structure represented by the general formula for the oligomeric mixture with n=2.

Activities of Dimer and Trimer Components

The dimer, trimer and tetramer components derived from 7-(2-(trans-4,4-dimethyl-3-keto-1-octenyl)-5-oxocyclopentenyl)-heptanoic acid designated as XXI in FIGS. 20–23 exhibit higher levels of activity in the protection of oxidative phosphorylation and ionophoretic activity in rat liver mitochondria as shown in Table 2 below. This table indicates the use of $PGB_x$ mixture as the standard representing 100% level both for the protection of oxidative phosphorylation of rat liver mitochondria (Samples tested at 7.4 μG/mL) and ionophoretic of rat liver mitochondria (samples tested at 30 μM) activities.

TABLE 2
PROTECTION OF OXIDATIVE PHOSPHORYLATION AND IONOPHORETIC ACTIVITY OF DIMERS, TRIMERS AND TETRAMERS OF 15-KETO PGB$_1$ AND 16, 16' DIMETHYL 15-KETO PGB$_1$

| COMPOUND | PROTECTION OF OXIDATIVE PHOSPHORYLATION | IONOPHORETIC ACTIVITY |
|---|---|---|
| PGB$_x$ | 100% | 100% |
| Monomer-Dimethyl PGB$_1$ | 0 | 0 |
| Dimer-Dimethyl PGB$_1$ | 110 | 270 |
| Trimer-Dimethyl PGB$_1$ | 125 | 215 |
| Tetramer-Dimethyl PGB$_1$ | 135 | 140 |

Oxidative Phosphorylation: RAT LIVER MITOCHONDRIA, Samples Tested at 7.4 μG/mL.
Ionophoretic Activity: RAT LIVER MITOCHONDRIA, Samples Tested 30 μM: micro molar As can be seen from Table 2 above, the oligomers such as dimer-dimethyl PGB$_1$; trimer-dimethyl PGB$_1$ and tetramerdimethyl PGB$_1$ have biological activities (i.e., the protection of oxidative phosphorylation of mitochondria and exhibiting ionophoretic activity) higher than the structurally undefined complex oligomeric mixture PGB$_x$ which was used as the standard to measure the biological activities of the oligomers. Oxidative phosphorylation and ionophoretic activity were measured for rat liver mictochondria wherein samples were tested at 7.4 micrograms per milliter (7.4 μg/mL) and 30 micro mole (30 μm) respectively.

Briefly describing the teachings of subject invention, structurally defined oligomers having biological activities (i.e., the protection of oxidative phosphorylation of mitochondria and which exhibit ionophoretic activity) are synthesized using a structurally defined precursor "C-16 blocked" 15-dehydro-PGB$_1$, i.e., 16,16-dimethyl-15-dehydro-PGB$_1$ and synthesis thereof.

Obviously, many modifications and variations of subject invention are possible in the light of the above teachings. For example, the reaction conditions may be varied without deviating from the teachings of subject invention. Furthermore, some of the steps in the synthesis of the oligomers and the precursor may be modified. It is therefore understood that within the scope of the appended claims the invention may be practiced otherwise than as specifically described.

What is claimed is:

1. A structurally defined oligomeric mixture exhibiting the protection of oxidative phosphorylation in mitochondria and ionopheretic activity prepared from a precursor of formula:

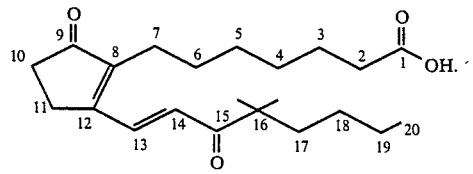

said oligomeric mixture being represented by a general structural formula:

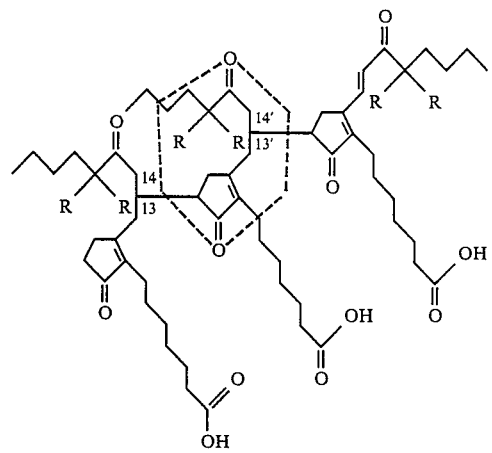

wherein n=0, 1, 2, 3 ... and R is CH$_3$.

2. A dimer fraction exhibiting the protection of oxidative phosphorylation in mitochondria and ionophoretic activity prepared from the precursor of claim 1, said dimer fraction having been isolated by size exclusion chromatography and structurally represented by the structural formula of claim 1 wherein n=0.

3. A trimer fraction exhibiting the protection of oxidative phosphorylation in mitochondria and ionophoretic activity prepared from the precursor of claim 1, said trimer fraction having been isolated by size exclusion chromatography and structurally repressed by the structural formula of claim 1 wherein n=1.

4. A tetramer fraction exhibiting the protection of oxidative phosphorylation in mitochondria and ionophoretic activity prepared from the precursor of claim 1, said tetramer fraction having been isolated by size exclusion chromatography and structurally represented by the structural formula of claim 1 wherein n=2.

5. A method for making a biologically active oligomeric mixture and separating into components thereof using 7-(2-(trans-4, 4-dimethyl-3-keto-1-octenyl)-5-oxocyclopentenyl)heptanoic acid as a precursor, said method comprises the steps of:

dissolving 2 grams of said precursor in a 100 mL of ethanol in a 500 mL round bottom flask to form a solution; of concentration of 20 mg/mL;
adding 100 mL of 0.1N potassium hydroxide to said solution to give a final concentration of 10 mg/mL to start oligomeric reaction;
monitoring said oligomeric reaction using ultraviolet spectroscopy by following the disappearance of ultraviolet absorption at 296 nm due to said precursor;
stopping said oligomeric reaction when about 50% complete by acidification of said oligomeric mixture with 2N hydrochloric acid;
adding 200 mL of water to said oligomeric mixture;
extracting thrice said oligomeric mixture using 3×50 mL of dichloromethane (CH$_2$CCl$_2$);
removing dichloromethane from said oligomeric mixture under vacuum;
separating various components of said oligomeric mixture by using Sephadex LH-20 chromatography; and
analyzing components of said oligomeric mixture.

6. The method of claim 5 wherein said step of separating various components of said oligomeric mixture includes using gel permeation in chromatography using three 2.54 cm×109 cm columns, in series, packed with Sephadex LH-20 with methanol used for elution to obtain 30% by weight of dimer (n=0), 20% by weight of trimer (n=1), less than 5% by weight of tetramer (n=2), and 45% by weight of unreacted precursor.

* * * * *

UNITED STATES PATENT AND TRADEMARK OFFICE
CERTIFICATE OF CORRECTION

PATENT NO. : 4,833,271

DATED : 23 May 1989

INVENTOR(S) : GEORGE L. NELSON

It is certified that error appears in the above-identified patent and that said Letters Patent is hereby corrected as shown below:

On the Title page please insert

--Assignee: The United States of America as represented by the Secretary of the Navy, Washington, D.C.--

Signed and Sealed this

Thirty-first Day of August, 1993

*Attest:*

BRUCE LEHMAN

*Attesting Officer*     Commissioner of Patents and Trademarks